(12) United States Patent
Sita et al.

(10) Patent No.: US 7,041,759 B2
(45) Date of Patent: May 9, 2006

(54) METHOD FOR THE PREPARATION OF WELL-DEFINED METAL ACETAMIDINATE-BASED CATALYSTS ON SOLID SUPPORTS

(75) Inventors: Lawrence R. Sita, Silver Spring, MD (US); Yonghui Zhang, College Park, MD (US)

(73) Assignee: The University of Maryland, College Park, College Park, MD (US)

( * ) Notice: Subject to any disclaimer, the term of this patent is extended or adjusted under 35 U.S.C. 154(b) by 0 days.

(21) Appl. No.: 10/716,604

(22) Filed: Nov. 20, 2003

(65) Prior Publication Data
US 2004/0110632 A1 Jun. 10, 2004

Related U.S. Application Data

(60) Provisional application No. 60/427,790, filed on Nov. 20, 2002.

(51) Int. Cl.
C08F 4/52 (2006.01)
C08F 4/76 (2006.01)

(52) U.S. Cl. .............. 526/172; 526/161; 526/134; 526/133; 526/127; 526/130; 526/904; 526/943; 526/348; 502/103

(58) Field of Classification Search ........... 526/161, 526/172, 130, 134, 904; 556/53, 52; 502/113, 502/103
See application file for complete search history.

(56) References Cited

U.S. PATENT DOCUMENTS

| | | | |
|---|---|---|---|
| 5,318,935 A | 6/1994 | Canich et al. | 502/117 |
| 5,387,660 A | 2/1995 | Doyle et al. | 526/69 |
| 5,502,128 A * | 3/1996 | Flores et al. | 526/160 |
| 5,527,752 A * | 6/1996 | Reichle et al. | 502/117 |
| 5,648,438 A | 7/1997 | Henry et al. | 526/65 |
| 5,674,795 A | 10/1997 | Wasserman et al. | 502/9 |
| 5,681,908 A | 10/1997 | Mehra et al. | 526/68 |
| 5,912,202 A | 6/1999 | Oskam et al. | 502/104 |
| 6,579,998 B1 * | 6/2003 | Sita et al. | 556/53 |
| 2004/0186253 A1 * | 9/2004 | Sita | 526/170 |
| 2004/0198930 A1 * | 10/2004 | Sita et al. | 526/113 |

FOREIGN PATENT DOCUMENTS

WO WO 01/30858 A1 * 5/2001
WO WO 03/008459 A1 1/2003

OTHER PUBLICATIONS

Jayaratne et al. J. Am. Chem. Soc. 2001, 123, 10754-10755.*
Keaton et al. J. Am. Chem. Soc. 2001, 123, 6197-6198.*
Keaton et al. J. Am. Chem. Soc. 2000, 122, 12909-12910.*
Jayaratne et al. J. Am. Chem. Soc. 2000, 122, 10490-10491.*

Abiko, A., et al., "Mechanism of the Double Aldol Reaction: The First Spectroscopic Characterization of a Carbon-Bound Boron Enolate Derived from Carboxylic Esters," *J. Am. Chem. Soc.* 124:10759-10764, American Chemical Society (Published on Web Aug. 15, 2002).

Asakura, T., et al., "Carbon-13 NMR Spectral Assignment of Five Polyolefins Determined from the Chemical Shift Calculation and the Polymerization Mechanism," *Macromolecules* 24:2334-2340, American Chemical Society (1991).

Barker, J., and Kilner, M., "The coordination chemistry of the amidine ligand," *Coord. Chem. Rev.* 133:219-300, Elsevier Science S.A. (1994).

Coles, M.P., and Jordan, R.F., "Cationic Aluminum Alkyl Complexes Incorporating Amidinate Ligands. Transition-Metal-Free Ethylene Polymerization Catalysts," *J. Am. Chem. Soc.* 119:8125-8126, American Chemical Society (1997).

Davies, S.G., "Organometallics as Nucleophiles," in *Organotransition Metal Chemistry: Applications to Organic Synthesis*, vol. II., Baldwin, J.E., ed., Pergamon Press, Oxford, Great Britain, pp. 187-217 (1982).

Edelmann, F.T., "N-silylated benzamidines: versatile building blocks in main group and coordination chemistry," *Coord. Chem. Rev.* 137:403-481, Elsevier Science S.A. (1994).

Hlatky, G.G., "Heterogeneous Single-Site Catalysts for Olefin Polymerization," *Chem. Rev.* 100:1347-1376, American Chemical Society (2000).

(Continued)

Primary Examiner—David W. Wu
Assistant Examiner—Rip A. Lee
(74) Attorney, Agent, or Firm—Sterne, Kessler, Goldstein & Fox P.L.L.C.

(57) ABSTRACT

An olefin polymerization pre-catalyst, an activated catalyst and a process for preparing the catalysts are described herein. The pre-catalyst has the formula:

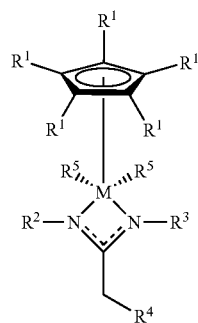

wherein the groups M and $R^1$–$R^4$ are defined herein. The group $R^4$ includes a solid-support.

34 Claims, 1 Drawing Sheet

OTHER PUBLICATIONS

Jayaratne, K.C., and Sita, L.R., "Stereospecific Living Ziegler-Natta Polymerization of 1-Hexene," *J. Am. Chem. Soc. 122*:958-959, American Chemical Society (2000).

Jayaratne, K.C., et al., "Living Ziegler-Natta Cyclopolymerization of Nonconjugated Dienes: New Classes of Microphase-Separated Polyolefin Block Copolymers via a Tandem Polymerization/Cyclopolymerization Strategy," *J. Am. Chem. Soc. 122*: 10490-10491, American Chemical Society (2000).

Keaton, R.J., et al., "Structural Characterization of Zirconium Cations Derived from a Living Ziegler-Natta Polymerization System: New Insights Regarding Propagation and Termination Pathways for Homogenous Catalysts," *J. Am. Chem. Soc. 122*:12909-12910, American Chemical Society (2000).

Keaton, R.J., et al., "Dramatic Enhancement of Activities for Living Ziegler-Natta Polymerizations Mediated by "Exposed" Zirconium Acetamidinate Initiators: The Isospecific Living Polymerization of Vinylcyclohexane," *J. Am. Chem. Soc. 123*:6197-6198, American Chemical Society (Published on Web Jun. 1, 2001).

Kim, Y.H., et al., "α-Iminoenamido Ligands: A Novel Structure for Transition-Metal Activation," *Organometallics 21*:3082-3084, American Chemical Society (Published on Web Jun. 18, 2002).

Koterwas, L.A., et al., "Stereospecific Syntheses, Metal Configurational Stabilities, and Conformational Analyses of meso-(R,S)- and (R,R)-($n^5$-$C_5R_5$)Ti($CH_3$)$_2$-$N_1$N-bis(1-phenylethyl)acetamidinates for R=H and Me," *Organometallics 18*:4183-4190, American Chemical Society (1999).

Neculai, A.M., et al., "Synthesis of New β-Diketiminato Complexes of Scandium(III): Unprecedented Formation of a Multicyclic Aggregate," *Organometallics 20*:5501-5503, American Chemical Society (Published on Web Nov. 22, 2001).

Okeya, S., et al., "Dinuclear platinum(II) complex bridged by an acetylacetonate(3—)anion," *J. Organomet. Chem. 551*:117-123, Elsevier Science S.A. (1998).

Sita, L.R., and Babcock, J.R., "Rapid Access to Dimethylcyclopentadienyltitanium(IV) Amidinate, ($C_5R_5$) TiMe$_2$[NR$^1$C(R$^2$) NR$^3$] (R=H and Me; R$^2$ =Me), Libraries," *Organometallics 17*:5228-5230, American Chemical Society (1998).

Woo, H-G., et al., "Synthesis, Characterization, and Reactivity of Triphenylsilyl, Triphenylgermyl, and Triphenylstannyl Derivatives of Zirconium and Hafnium," *Organometallics 11*:2198-2205, American Chemical Society (1992).

Co-pending U.S. Appl. No. 10/484,210, inventors Sita et al., filed Jan. 20, 2004.

Zhang, Y. and Sita, L.R., "Solid-supported stereospecific living Ziegler-Natta polymerization of α-olefins," *Chem. Commun. 18*:2358-2359, The Royal Society of Chemistry (Sep., 2003).

Jayaratne et al. J. Am Chem. Soc. 20000, 122, 958-959.*

Koterwas et al. Organometallics 1999, 18, 4183-4190.*

Sita et al. Organometallics 1998, 17, 5228-5230.*

* cited by examiner

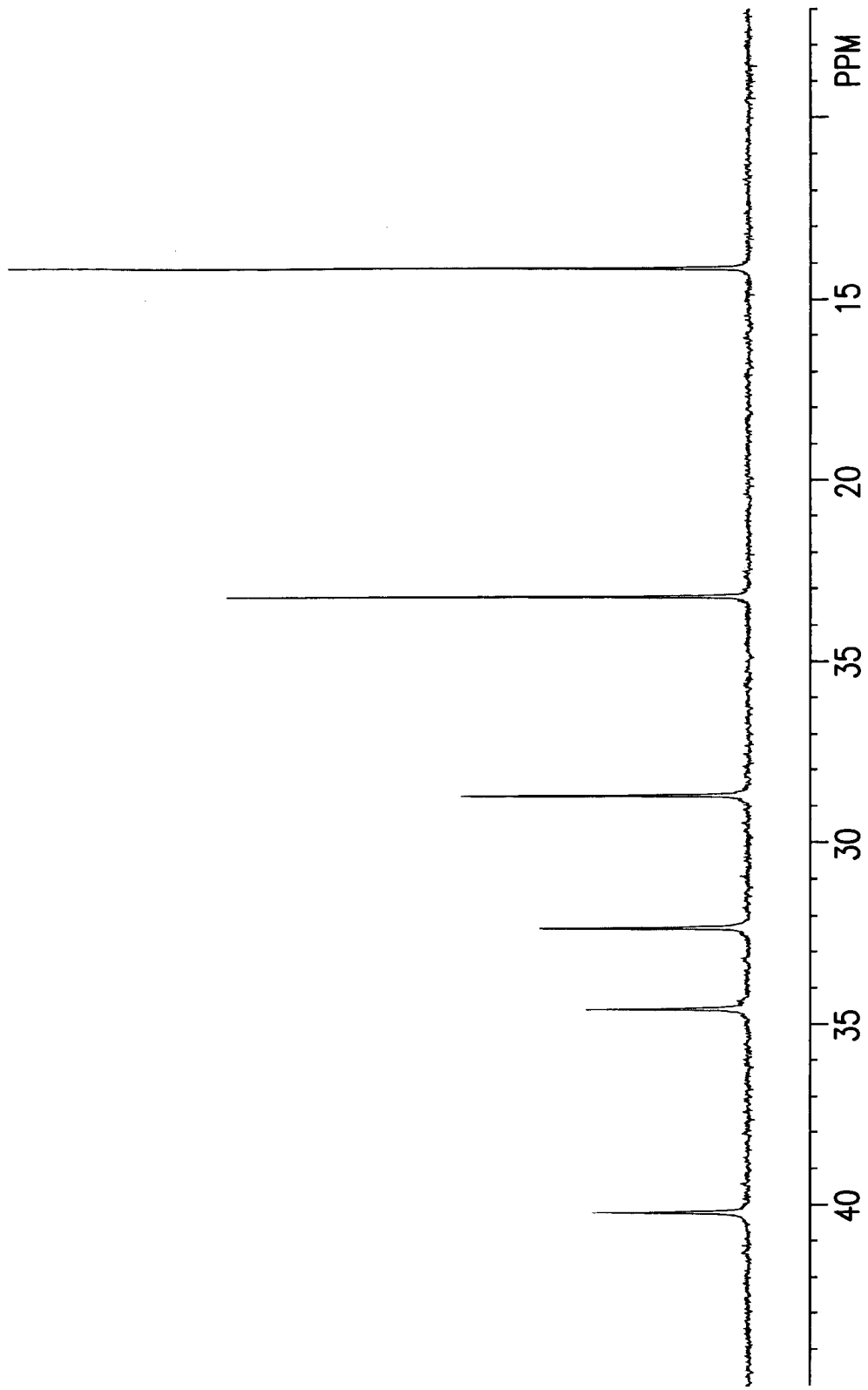

METHOD FOR THE PREPARATION OF WELL-DEFINED METAL ACETAMIDINATE-BASED CATALYSTS ON SOLID SUPPORTS

Part of the work performed during development of this invention utilized U.S. Government funds. The work was partly funded by the National Science Foundation Grant CHE-0092493. The U.S. Government has certain rights in this invention.

BACKGROUND OF THE INVENTION

1. Field of the Invention

The present invention relates to novel olefin polymerization catalysts that have the ability to polymerize a variety of α-olefins in a stereospecific and living fashion.

2. Related Art

The amidinate ligand fragment, —[N(R$^1$)C(R$^2$)N(R$^3$)]—, is a structural component found within a diverse range of mononuclear transition-metal and main-group-metal complexes (Barker, J. and Kliner, M., *Coord. Chem. Rev.* 133: 219–300 (1994); Edelmann, F. T., *Coord. Chem. Rev.* 137: 403–481 (1994)). Synthetic methods available for the incorporation of this group into the coordination sphere of metals, however, still remain quite limited, and these include (1) classical salt elimination using metal halides and alkalimetal amidinates, (2) condensation between metal halides and silyl-substituted amidines, and (3) carbodiimide insertion into metal-carbon bonds. (Coles, M. P., and Jordan, R. F., *J. Am. Chem. Soc.* 119:8125–8126 (1997); Sita, L. R., and Babcock, J. R., *Organometallics* 17:5228–5230 (1998); Korerwas, L. A., et al., *Organometallics* 18:4183–4190 (1999)).

Recently, it was documented that d$^0$ group 4 mono(cyclopentadienyl)metal amidinates of the general formula (η$^5$—C$_5$R$_5$)MXY[N(R$^1$)C(R$^2$)N(R$^3$)] (M=Zr, R=H, Me, X=Y=Me, R=Me) are highly active precatalysts for the stereoselective living polymerization of a wide variety of α-olefins and α,ω-nonconjugated dienes upon activation with a borate cocatalyst, such as [Ph$_3$C][B(C$_6$F$_5$)$_4$] (Jayaratne, K. C. and Sita, L. R. *J. Am. Chem. Soc.* 122: 958–959 (2000); Jayaratne, K. C., et al., *J. Am. Chem. Soc.* 122:10490–10491 (2000); Keaton, R. J., et al., *J. Am. Chem. Soc.* 123:6197–6198 (2001)). Further development of these catalysts is nevertheless needed in order to optimize their catalytic potential. Structure/property relationships must be further studied and heterogenization of the class of Ziegler-Natta precatalyst on solid supports must be developed (Hlatky, G. G., *Chem. Rev.* 100:1347–1376 (2000)). However, this requires derivatives of the amidinate catalysts that are not readily prepared through the conventional methods enumerated above. Therefore, new methods of derivatizing amidinate metallocene catalysts are needed in order to produce more efficient catalysts.

SUMMARY OF THE INVENTION

Described herein is a new synthetic procedure that circumvents this problem by providing rapid access to a number of new acetamidinate metal complexes through the deprotonation and chemoselective functionalization of an acetamidinate fragment within a metal complex. Just as the direct deprotonation of η$^5$-cyclopentadienyl and η$^6$-arene metal complexes have provided new generations of these ligand types (Davies, S. G., *Organotransition Metal Chemistry: Applications to Organic Synthesis*, Pergamon Press, New York, N.Y. (1982)), the synthetic methods of the present invention are of general use for extending the scope of amidinate-based metal complexes.

In one embodiment, the present invention relates to an olefin polymerization catalyst comprising a pre-catalyst having the formula:

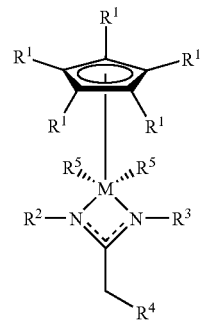

wherein M is Ti, Zr or Hf;

each R$^1$ is independently hydrogen or alkyl or two adjacent R$^1$ form an aryl group;

each R$^2$ and R$^3$ is optionally substituted and is independently alkyl, cycloalkyl, SiX$_3$, or aryl; or one R$^1$ and one of R$^2$ or R$^3$ are taken together to form an alkyl, aryl, arylalkyl or alkylarylalkyl bridge;

R$^4$ comprises alkyl, cycloalkyl, SiX$_3$, aryl, BR$^6_3$ or a solid support;

each R$^5$ is halo, optionally substituted alkyl, cycloalkyl, aryl, or arylalkyl;

R$^6$ is optionally substituted phenyl;

B is the element boron; and

X is independently halo, alkyl, alkoxy or aryl.

In another embodiment, the present invention relates to a process for preparing an olefin polymerization catalyst, comprising deprotonating a metal acetamidinate having the formula:

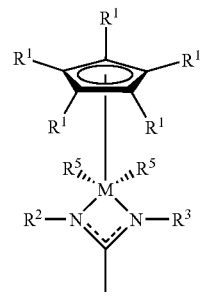

to form an intermediate; and contacting the intermediate with an electrophile to form a precatalyst. Preferably, the electrophile comprises a solid support, resulting in a solid-supported pre-catalyst. In a preferred embodiment, the process further comprises reacting the pre-catalyst with an activating co-catalyst to form an activated olefin polymerization catalyst.

In another embodiment, the present invention relates to a process for preparing a polyolefin, comprising reacting an olefin with an activated olefin polymerization catalyst composition, under conditions that result in the formation of a polyolefin; wherein the catalyst composition comprises a pre-catalyst of the present invention and a co-catalyst having one of the formulae:

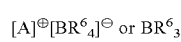

wherein A$^⊕$ is a cationic Lewis or Brønsted acid.

BRIEF DESCRIPTION OF THE FIGURES

FIG. 1 shows the $^{13}C\{^1H\}$ Nuclear Magnetic Resonance (NMR) (100 MHz, $CDCl_3$) spectrum of isotactic poly(1-hexene) prepared in accordance with the present invention.

DETAILED DESCRIPTION

As used herein, "alkyl" refers to straight- or branched-chain hydrocarbons having from 1 to 10 carbon atoms and more preferably 1 to 8 carbon atoms, including by way of example methyl, ethyl, propyl, i-propyl and t-butyl.

"Aryl" by itself or as part of another group refers to monocyclic, bicyclic or tricyclic aromatic groups containing 6 to 14 carbon atoms in the ring position. Useful aryl groups include $C_{6-14}$ aryl, preferably $C_{6-10}$ aryl. Typical $C_{6-14}$ aryl groups include phenyl, naphthyl, indenyl, phenanthrenyl, anthracenyl, fluorenyl and biphenyl groups.

"Optionally substituted aryl" refers to an aryl group, wherein the aryl ring or rings may contain 1 to 5 electron donating or electron withdrawing groups. By way of example, electron donating groups include, but are not limited to alkoxy, amide, aryl and alkyl. Examples of electron withdrawing groups include, but are not limited to, halo, ketone, ester, aldehyde, cyano and nitro.

"Arylalkyl" refers to an alkyl group mentioned above substituted by a single aryl group including, by way of example, benzyl, phenethyl and naphthylmethyl.

"Cycloalkyl" refers to cyclic alkyl groups containing between 3 and 8 carbon atoms having a single cyclic ring including, by way of example, cyclopropyl, cyclobutyl, cyclopentyl, cyclooctyl and the like.

"Alkylarylalkyl" refers to an alkyl group mentioned above substituted by a single aryl group, wherein the aryl group is further substituted by one or more alkyl groups. Examples include, without limitation, 4-methylbenzyl and 4-ethylphenethyl.

"Halo" refers to fluoro, chloro, bromo and iodo.

As used herein, the term "polyolefin" comprises olefin homooligomers, homopolymers, co-polymers and block copolymers.

Examples of "solid supports" include, among other things, inorganic oxide support materials, including but not limited to talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels. Solid support also includes organic solid supports, including but not limited to polystyrene, functionalized polystyrene, polyamides such as nylon and polysaccharides such as cellulose.

Solid supports can be in any form that allows for covalent bonding of catalyst molecules to the solid support and results in an active olefin polymerization catalyst. Specific examples include, but are not limited to spheres, rods and other shaped particles, beads and planar surfaces.

"Anchored to the solid support" is used herein to mean that a covalent bond is formed between the acetamidinate metallocene catalyst molecule and the solid support. It is understood by one of ordinary skill in the art that each solid support molecule or polymer can be prepared to have a plurality of organometallic catalyst molecules covalently bonded to it. Solid supports can be prepared having about 0.01–100 mequiv/g catalytic sites, about 0.1–50 mequiv/g of catalytic sites or about 0.1–10 mequiv/g of catalytic sites. Catalytic site is used herein to refer to an acetamidinate metallocene catalyst molecule.

"Linking group" is used herein to mean any functional group that is used to anchor the acetamidinate catalyst to the solid support. The linking group is covalently bonded to the solid support and to the acetamidinate catalyst molecule. In a preferred embodiment, the linking group includes, but is not limited to sulfonyl, alkyl, alkoxy, carbonyl, amino, epoxy, thio and aryl or does not exist.

"Electrophile" is used herein to mean any chemical functional group, molecule or atom that is electron-deficient or has partial or full positive charge. "Nucleophile" is used herein to mean any chemical functional group, molecule or atom that is electron-rich or has excess partial or full negative charge. "Leaving group" is used herein to mean any atom, functional group or molecule that can be displaced from a substrate by another atom, functional group or molecule in a substitution reaction. Specific examples of leaving groups include, but are not limited to halo, perfluoroalkylsulfonato, alkylsulfonato, perfluoroalkylcarboxy and alkoxy.

Activated olefin polymerization catalysts that contain an enantiomeric excess of one enantiomer or that are substantially enantiopure may also be prepared from the precatalyst. Such optically active catalysts allow one to control the absolute handedness of the polyolefins and block co-polymers of the invention. In this embodiment, the precatalyst contains one or more optically active substituents, i.e., those containing chiral centers of absolute configuration, at $R^1$, $R^2$, $R^3$ and $R^4$.

Ligands with enolizable protons can be functionalized prior to metal complexation by deprotonation with a strong base followed by reaction with an electrophile. One may functionalize a metal-complexed ligand containing enolizable protons through the same process, and this includes metal complexes containing the acetylacetonato (acac) ligand (Okeya, S., et al., *J. Organomet. Chem.* 551:117–123 (1998); Neculai, A. M., et al., *Organometallics* 20:5501–5503 (2001)).

As shown in Scheme 1, complexes 1a (M=Zr) and 1b (M=Hf) were selected for derivatization via deprotonation using a base. Bases for use in the present invention include any non-nucleophilic base capable of removing a proton from the acetamidinate ligand. Such bases include but are not limited to, sterically hindered bases, for example, lithium triphenylsilane, $LiSiPh_3$ and potassium bis(trimethylsilyl)amide, $KN(SiMe_3)_2$. Alternative bases include alkali alkyl and alkali aryl bases, such as tert-butyl lithium, phenyllithium and hindered alkali alkoxides such as potassium tert-butoxide. The deprotonation is carried out in a solvent. Suitable solvents for use include, but are not limited to ethers, aromatic and non-aromatic hydrocarbons and others. Specific examples include, but are not limited to tetrahydrofuran, diethyl ether, hexane, benzene and toluene. The deprotonating reaction can be carried out at any temperature that results in the formation of a deprotonated intermediate. For example, the reaction may be carried out at a temperature in the range of about −10° C. to about 50° C., preferably, about 10° C. to about 30° C.

As shown in Scheme 1, $LiSiPh_3$ was successfully employed, and can easily be obtained in crystalline form as its tetrahydrofuran (THF) adduct (Woo, H. G., et al., *Organometallics* 11:2198–2205 (1992)). More specifically, the deprotonation reaction of 1a with a slight excess of $LiSiPh_3$ in THF at 25° C. yielded, upon removal of the solvent after about 2 h, a near-quantitative yield of complex 2a, which was isolated as a purple powder. Use of the less hindered base $LiSiMe_2Ph$ led to preferential nucleophilic attack at the metal center, rather than deprotonation, to provide a zirconium silyl complex. For the hafnium analogue 1b, deprotonation to provide 2b was achieved using $KN(SiMe_3)_2$ rather than $LiSiPh_3$.

SCHEME 1

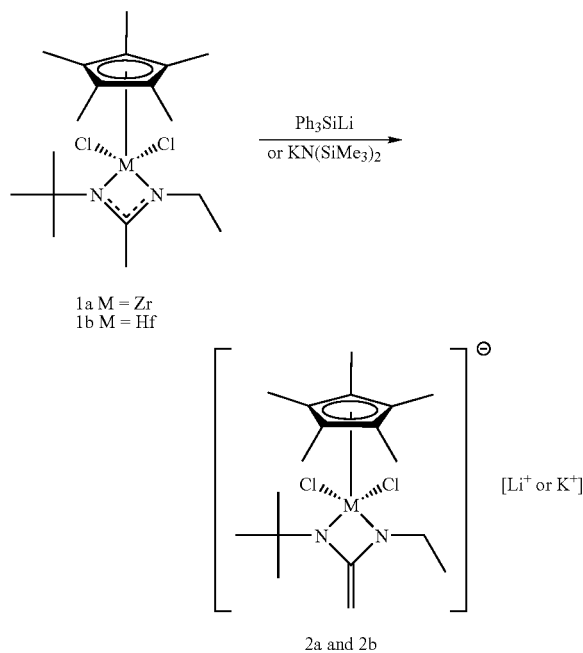

1a M = Zr
1b M = Hf 2a and 2b $^1$H and $^{13}$C NMR spectra taken in THF-d$_8$ support the enolate structure for the deprotonated intermediates 2a–b shown in Scheme 1. The deprotonated intermediates 2a–b are serving as dianionic ligands. Thus, a $^1$H NMR (400 MHz, 25° C.) spectrum of 2a in this solvent displays a set of two resonances at δ 2.91 and 2.89 ppm for the diastereotopic methylene protons of the enolized acetamidinate fragment. Both of these protons were found to correlate, via a 2D $^{13}$C—$^1$H HSQC NMR spectrum, with a $^{13}$C NMR resonance at 55.6 ppm ($^1$J($^{13}$C—$^1$H)=157 Hz). The observation that the $^2$J($^1$H—$^1$H) coupling constant between these protons is smaller than the line width of the resonances is consistent with the $^1$H NMR data reported for other enolates (Abiko, A., et al., *J. Am. Chem. Soc.* 124:10759–10764 (2002)).

As shown in Scheme 2, in aprotic polar coordinating solvents, such as diethyl ether (Et$_2$O), 2a can undergo loss of LiCl to produce neutral, solvent-stabilized species such as 3. Indeed, upon attempts to grow crystals of 2a from a Et$_2$O/pentane solvent mixture, continual precipitation of LiCl was observed to occur and subsequent single-crystal X-ray analysis of the dark orange crystalline material that was obtained revealed it to be the dinuclear species 4. Species 4 can arise from dimerization of 3 upon displacement of the weakly coordinated solvent molecule.

SCHEME 2

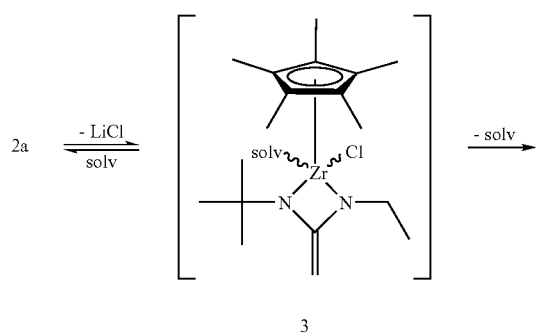

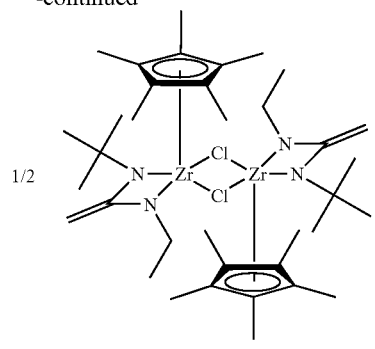

4

The methylene carbon of the enolized acetamidinate, C12, is trigonal coplanar, as revealed by the sum of the bond angles about this atom, $\Sigma\theta_{C12}$, which is 360°, and the C11–C12 bond length of 1.332(8) Å supports full double-bond character for the interaction between these two carbon centers.

As shown in Scheme 3, deprotonated intermediates 2a and 2b were reacted with a variety of electrophiles. The electrophiles are denoted E-Q, wherein Q is a leaving group. In electrophiles (a)–(c), the leaving group is chloride ion. For (a)–(c), therefore, the resulting R$^4$ is benzyl, chloromethyl and chlorodimethylsilyl, respectively. In (d), Q does not exist, and the resulting product is a zwitterionic complex, wherein R$^4$ is B(C$_6$F$_5$)$_3$. The reaction successfully placed a substituent at the enolized carbon of the acetamidinate ligand. The products of these reactions provide new types of acetamidinate precatalysts that are not readily accessible by conventional synthetic procedures. These novel products include, but are not limited to, compounds 5a–d (M=Hf).

SCHEME 3

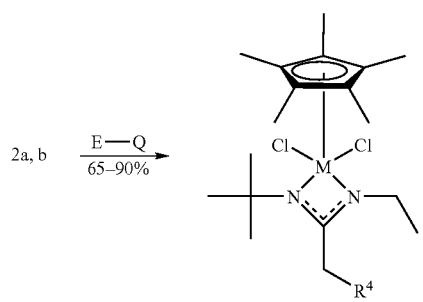

E—Q = (a) PhCH$_2$Cl, (b) CH$_2$Cl$_2$,
(c) Me$_2$SiCl$_2$, (d) B(C$_6$F$_5$)$_3$

The chlorodimethylsilyl group in 5c provides a convenient handle by which to anchor this species to solid supports. Solid supports substituted with nucleophilic groups can react with the chlorodimethylsilyl group, to form a covalent bond between the nucleophilic group of the solid support and the acetamidinate metallocene catalyst. In a specific example, solid supports having hydroxyl groups can react with the chlorodimethylsilyl group to form a covalent silicon-oxygen bond between the solid support and the acetamidinate catalyst with HCl as a by-product. Using this technique, solid-supported catalysts can be readily prepared. Any method known to one of ordinary skill in the art can be used to anchor species such as 5c to a support. For example, species 5c may be anchored to an inorganic oxide particle by heating a solution of 5c with oxide particles to a temperature sufficient to form a covalent bond between species 5c and the oxide particle. Because oxide particles have a plurality of nucleophilic hydroxyl groups, a plurality of acetamidinate metallocene catalysts can be anchored to a single inorganic oxide particle. Following this strategy, an example of a solid-supported polymerization catalyst has the formula:

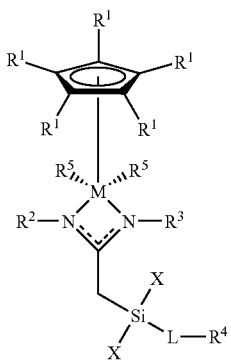

wherein L is a linking group.

In a preferred embodiment, L is amino, epoxy, thio, alkyl or aryl.

Catalyst molecules of the present invention can also be anchored to organic polymer supports. Organic polymers can be functionalized with a variety of electrophilic linking groups that will react with deprotonated intermediates of the present invention, such as 2a–b, to give solid-supported pre-catalysts. A plurality of acetamidinate metallocene catalysts may be covalently bonded to an organic polymer support.

Polystyrene-supported pre-catalysts can be prepared having the formula:

poly[A-co-B];

wherein unit A has the formula:

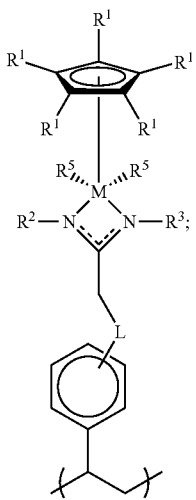

unit B has the formula:

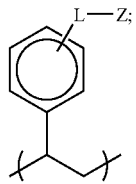

L is a linking group; and
Z is hydrogen, $C_{1-3}$ alkyl or $C_{1-3}$ alkoxy.

In a preferred embodiment, L is sulfonyl, $C_{1-3}$ alkyl, $C_{1-3}$ alkoxy, carbonyl or does not exist. Unit A can have a molar percentage from about 10–100%. Preferably, unit A has a molar percentage in the range of about 50–80% and unit B has a molar percentage in the range of about 20–50%. Polystyrene may be functionalized with a plurality of electrophiles to form electrophilic polystyrene. Examples of electrophilic polystyrene include, but are not limited to chloromethylated- and sulfonyl chloride substituted-polystyrene. In a specific example, chloromethylated polystyrene beads (1.3 mequiv/g of chloromethyl groups) were reacted with deprotonated intermediate 2a to produce a polystyrene-supported catalyst in which 70% of the chloromethyl sites were found to have reacted.

Referring back to Scheme 3, the enolates 2a and 2b were reacted with a group 13 Lewis acid co-catalyst to produce charge-neutral zwitterionic complexes that could then function as activated Ziegler-Natta polymerization initiators (Kim, Y. H., et al., *Organometallics* 21:3082–3084 (2002)). Treatment of a $Et_2O$ solution of 2a with 1 equiv of $B(C_6F_5)_3$ provided complex 5d. Upon crystallization from solution at −30° C., the $Et_2O$-coordinated zwitterionic complex was isolated in 66% yield. The structural environment around the zirconium atom is very similar to that observed for the solid-state structure of an $Et_2O$ complex of a cationic zirconium acetamidinate that is a known active initiator for olefin polymerization (Keaton, R. J., et al., *J. Am. Chem. Soc.* 122:12909–12910 (2000)). Therefore complex 5d can act as an olefin polymerization catalyst and no additional activating co-catalyst is necessary.

The reaction of the deprotonated intermediate with an electrophile forms an olefin polymerization precatalyst, preferably, a solid-supported olefin polymerization precatalyst. The pre-catalyst is converted to an activated olefin polymerization catalyst by reacting it with an activating co-catalyst. The activated olefin polymerization catalyst thus produced is useful in the polymerization of a variety of α-olefins in a stereospecific and living fashion. For example, 1-hexene and vinylcyclohexane are each polymerized by an activated olefin polymerization catalyst of the present invention to give a highly isotactic and high molecular weight material. In addition, the same catalyst polymerizes both 1-hexene and vinylcyclohexane in a living fashion. Other α-olefins that may be polymerized with a catalyst of the present invention include, but are not limited to γ-substituted alpha olefins such as 3-methylbutene, 3-methyl-1-pentene, vinylcyclohexene, vinylcyclobutane, vinylcyclopentane, vinylcyclooctane, 1-decene and enantiomerically pure β-citronellene.

The activating co-catalyst is capable of generating the activated olefin polymerization catalyst. Preferably, the activating co-catalyst is one of the following: (a) ionic salts of the general formula $[A^+][^-BR^6_4]$, or (b) a boron alkyl of the general formula $BR^6_3$.

Examples of Lewis or Brønsted acids that may be used in the practice of the invention include, but are not limited to tetra-n-butylammonium, triphenylcarbonium and dimethylanilinium cations.

The molar ratio of olefin polymerization pre-catalyst to activating co-catalyst usefully employed in the olefin polymerization catalyst composition may vary. When the activating co-catalyst is an ionic salt of the formula $[A^+][^-BR^6_4]$, or a boron alkyl of the formula $BR^6_3$, the molar ratio of boron atoms contained in the ionic salt or the boron alkyl to total metal atoms contained in the olefin polymerization pre-catalyst is generally in the range of from about 0.9:1 to about 1.5:1, preferably in the range of from about 1:1 to about 1.1:1.

Reaction of the olefin polymerization pre-catalyst with the activating co-catalyst may typically take place within about 10 seconds to about 30 minutes, most preferably within about 1 to about 10 minutes, at temperatures of about −35 to about 25° C., preferably about −10 to about 0° C.

The polymerization reaction preferably takes place in a liquid medium. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are chlorobenzene, dichlorobenzene, isopentane, hexane, cyclohexane, heptane, benzene, toluene, trifluorotoluene, pentane, octane, isooctane, dichloromethane and the like. Reactive contact between the olefin monomer and the catalyst composition may be maintained by constant stirring or agitation. The reaction medium containing the olefin polymer product and unreacted olefin monomer may be withdrawn from the reactor continuously. The olefin polymer product may be separated, and the unreacted olefin monomer and liquid reaction medium may be recycled into the reactor.

U.S. Pat. No. 5,912,202 teaches that polymerization may be carried out in a single reactor or in two or more reactors in series, and is conducted substantially in the absence of catalyst poisons. According to U.S. Pat. No. 5,681,908 catalyst poisons may include water, oxygen, carbon dioxide, hydrogen, sulfur and acetylene. U.S. Pat. No. 5,674,795 teaches that even minor amounts (i.e., ≦2 ppm) of such materials have been found to affect the polymerization adversely. According to the present invention, organometallic compounds may be employed as scavenging agents for poisons and to increase the catalyst activity. Examples of scavenging agents are metal alkyls, preferably aluminum alkyls, most preferably triisobutylaluminum.

Conventional adjuvants may be included in the process, provided they do not interfere with the operation of the activated olefin polymerization catalyst composition in forming the desired polyolefin. Hydrogen or a metal or non-metal hydride, e.g., a silyl hydride, may be used as a chain transfer agent in the process.

Polyolefins that may be produced according to the invention include, but are not limited to, those made from olefin monomers such as ethylene and linear or branched higher α-olefin monomers containing 3 to about 20 carbon atoms. Homopolymers, co-polymers or block co-polymers of ethylene and such higher alpha-olefin monomers, with densities ranging from about 0.86 to about 0.95 may be made. In addition, homopolymers, co-polymers and block co-polymers that have high isotacticity and low polydispersities may be made. For example, high isotacticity, as determined using the pentad level of analysis, is from about 90 to 100 percent, preferably from about 97 to 100 percent (Asakura et al., *Macromolecules* 24:2334–2340 (1991)). Low polydispersity is, for example, from about 1.01 to 2.0. Suitable higher alpha-olefin monomers include, for example, propylene, 1-butene, 1-pentene, 1-hexene, 4-methyl-1-pehtene, 1-octene, 3,5,5-trimethyl-1-hexene, vinylcyclohexane, 3-methylbutene, 3-methyl-1-pentene, vinylcyclobutane, vinylcyclopentane, vinylcyclooctane, 1-decene and enantiomerically pure β-citronellene. Olefin polymers according to the invention may also be based on or contain conjugated or non-conjugated dienes, such as linear, branched, or cyclic hydrocarbon dienes having from about 4 to about 20, preferably 4 to 12, carbon atoms.

Preferred dienes include 1,4-pentadiene, 1,5-hexadiene, 5-vinyl-2-norbornene, 1,7-octadiene, vinylcyclohexene, dicyclopentadiene, butadiene, isobutylene, isoprene, ethylidene, norbornene and the like. Aromatic compounds having vinyl unsaturation such as styrene and substituted styrenes, vinyl trialkyl silanes and the like may be polymerized according to the invention as well. Specific polyolefins that may be made according to the invention include, for example, poly-1-hexene, polyvinylcyclohexane, 1-hexene/ vinylcyclohexane block co-polymers, polyethylene, polypropylene, ethylene/propylene rubbers (EPR's), ethylene/propylene/diene terpolymers (EPDM's), polybutadiene, polyisoprene and the like, as well as a variety of di- and ter-block co-polymers.

Having now generally described this invention, the same will be understood by reference to the following examples, which are provided herein for purposes of illustration only and are not intended to be limiting unless otherwise specified.

EXAMPLE I

Preparation of Cp*ZrCl$_2$[$^t$-BuNC(Me)NEt]

To 2.04 g (16.15 mmole) of 1-$^t$-butyl-3-ethyl-carbodiimide in 150 mL of Et$_2$O, 11.6 mL of MeLi (16.15 mmole) was added slowly at 0° C. via a syringe. The mixture was slowly warmed up to room temperature within 3 hr. The solution was transferred via cannula to Cp*ZrCl$_3$ (5.374 g, 16.15 mmole) in 150 mL of Et$_2$O at −78° C. The mixture was slowly warmed up to room temperature within 3 hr, and then stirred at room temperature for 12 hr. All volatiles were removed in vacuo and then toluene was used to extract the crude product from the mixture. Recrystallization from pentane at 30° C. provided analytically pure compound. Yield: 6.42 g (91%).

EXAMPLE II

Preparation of Solid-Supported Catalytic Beads

To a 50 mL tetrahydrofuran (THF) solution of Cp*ZrCl$_2$-[$^t$-BuNC(Me)NEt] (1.76 g, 4.0 mmole), 1.958 g (4.2 mmole) of LiSiPh$_3$(THF)$_3$ was added. The mixture was allowed to stir for 30 min, and then volatiles removed in vacuo. Toluene (50 mL) was added to the purple residue, followed by 2.94 g of chloromethylated polystyrene beads (Bio-Beads™ S-X1, 1.36 mequiv/g, available from Bio-Rad Laboratories, Hercules, Calif.). The resulting turbid mixture was stirred for 4 hr, and then filtered. The pale yellow solid was suspended in 100 mL of Et$_2$O and 6.48 mL of MeLi (17.47 mmole) was added via a syringe at −78° C. The mixture was allowed to warm up to room temperature within 3 hr, and then stirred at room temperature for 2 hr. The mixture was then filtered, and the solid beads were dried in vacuo. Yield: 3.80 g.

To 0.548 g of the beads, 20 mL of chlorobenzene was added, and the mixture was chilled down to −10° C. To this mixture, 0.40 g of [PhNHMe$_2$][B(C$_6$F$_5$)$_4$] (0.5 mmole) in 10 mL of chlorobenzene was added. The beads turned orange immediately, and were filtered and washed with cold chlorobenzene, toluene, pentane, and kept at −10° C. Yield: 0.794 g. Chemical analysis: F % 16.32 (corresponds to 0.41 mequiv/g of active catalytic sites).

EXAMPLE III

Polymerization of 1-hexene

To 10 mL of chlorobenzene, 79.4 mg of the beads was added and the mixture was chilled to −10° C. The 1-hexene (0.84 g) was quickly introduced and the mixture was stirred at −10° C. The polymerization was then quenched by acidic MeOH after 2 hr. The chlorobenzene was removed in vacuo, and CHCl$_3$ was used to extract the polymer from the beads. The extract was added to MeOH to precipitate the polymer. Mn/mw values were determined by GPC analysis (THF, 1.1 mL/min). M$_n$=40300, M$_w$=42700, PDI=1.06. Yield: 0.32 g (38.1%). FIG. 1, shows the NMR spectrum of the isolated poly(1-hexene). $^{13}$C($^1$H) NMR (100 MHz, CDCl$_3$): δ 40.21 (s), 34.59 (s), 32.36 (s), 28.71 (s), 23.23 (s), 14.19(s) (see attached).

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

What is claimed is:

1. An olefin polymerization catalyst comprising a pre-catalyst having the formula:

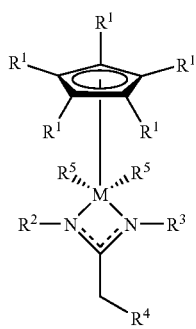

wherein M is Ti, Zr or Hf;
each R$^1$ is independently hydrogen or alkyl or two adjacent R$^1$ form an aryl group;
each R$^2$ and R$^3$ is optionally substituted and is independently alkyl, cycloalkyl, SiX$_3$, or aryl; or
one R$^1$ and one of R$^2$ or R$^3$ are taken together to form an alkyl, aryl, arylalkyl or alkylarylalkyl bridge;
R$^4$ comprises SiX$_3$, BR$^6_3$ or a solid support;

each R$^5$ is halo, optionally substituted alkyl, cycloalkyl, aryl, or arylalkyl;
R$^6$ is optionally substituted phenyl;
B is the element boron; and
X is independently halo, alkyl, alkoxy or aryl.

2. A catalyst composition comprising the olefin polymerization catalyst of claim 1 and a co-catalyst of the formula:

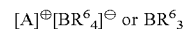

wherein A$^⊕$ is a cationic Lewis or Brønsted acid.

3. The composition of claim 2, wherein said co-catalyst is [PhNHMe$_2$][B(C$_6$F$_5$)$_4$].

4. The catalyst of claim 1, wherein said solid support is an organic polymer or inorganic oxide.

5. The catalyst of claim 4, wherein said organic polymer is a polystyrene, polyamide, or polysaccharide.

6. The catalyst of claim 4, wherein said inorganic oxide is a silica, alumina, titania, zirconia, or a combination thereof.

7. The catalyst of claim 1, wherein said aryl is phenyl, naphthyl, indenyl, phenanthrenyl, anthracenyl, fluorenyl, or biphenyl.

8. The catalyst of claim 1, wherein:
said optional substituents on alkyl are alkoxy, amide, aryl, alkyl, halo, ketone, ester, aldehyde, cyano and nitro; and
said optional substituents on aryl are alkoxy, amide, aryl, alkyl, halo, ketone, ester, aldehyde, cyano and nitro.

9. The catalyst of claim 1, wherein M is Zr.

10. The catalyst of claim 1, wherein each R$^1$ is hydrogen.

11. The catalyst of claim 1, wherein each R$^1$ is methyl.

12. The catalyst of claim 1, wherein said catalyst comprises about 0.1–10 mequiv/g of catalytic sites.

13. The catalyst of claim 1, wherein said pre-catalyst is a copolymer having the formula:

poly[A-co-B];

wherein unit A has the formula:

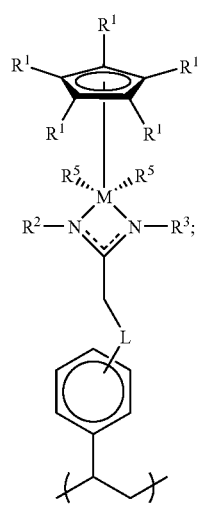

unit B has the formula:

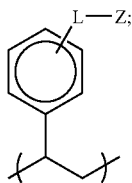

L is a linking group; and

Z is hydrogen, $C_{1-3}$ alkyl or $C_{1-3}$ alkoxy.

14. The catalyst of claim 13, wherein L is sulfonyl, $C_{1-3}$ alkyl, $C_{1-3}$ alkoxy, carbonyl or does not exist.

15. The catalyst of claim 13, wherein said unit A has a molar percentage in the range of about 50–80% and said unit B has a molar percentage in the range of about 20–50%.

16. The catalyst of claim 1, wherein said pre-catalyst has the formula:

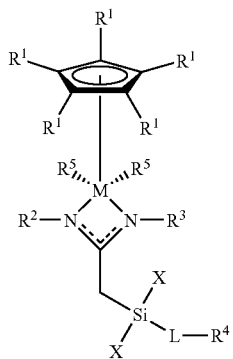

wherein L is a linking group.

17. The catalyst of claim 16, wherein L is amino, epoxy, thio, alkyl, alkoxy or aryl.

18. The catalyst of claim 16 wherein $R^4$ is an inorganic oxide and L is epoxy.

19. The catalyst of claim 16, wherein said catalyst comprises about 0.1–10 mequiv/g of catalytic sites.

20. A process for preparing an olefin polymerization catalyst, comprising:

(a) deprotonating a metal acetamidinate having the formula:

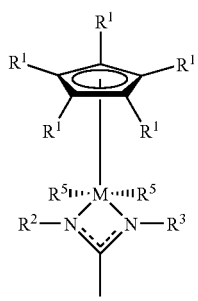

wherein M is Ti, Zr or Hf;

each $R^1$ is independently hydrogen or alkyl or two adjacent $R^1$ form an aryl group;

each $R^2$ and $R^3$ is optionally substituted and is independently alkyl, cycloalkyl, $SiX_3$, or aryl; or one $R^1$ and one of $R^2$ or $R^3$ are taken together to form an alkyl, aryl, arylalkyl or alkylarylalkyl bridge;

each $R^5$ is halo, optionally substituted alkyl, cycloalkyl, aryl, or arylalkyl;

X is independently halo, alkyl, alkoxy or aryl;

to form an intermediate; and (b) contacting said intermediate with an electrophile to form a precatalyst.

21. The process of claim 20, further comprising:

(c) reacting said pre-catalyst with an activating co-catalyst.

22. The process of claim 20, wherein said electrophile is electrophilic polystyrene.

23. The process of claim 20, wherein said electrophile is chloromethyl-substituted polystyrene, sulfonyl chloride-substituted polystyrene, $B(C_6F_5)_3$ or $SiX_3$; and X is independently halo, alkyl, alkoxy or aryl.

24. The process of claim 20, further comprising after (b):

(d) reacting said precatalyst with an inorganic oxide solid support.

25. The process of claim 20, wherein said inorganic oxide is a silica, alumina, titania, zirconia, or a combination thereof.

26. The process of claim 21, wherein said co-catalyst has one of the formulae:

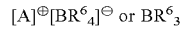

wherein $A^\oplus$ is a cationic Lewis or Brønsted acid;

B is the element boron; and $R^6$ is optionally substituted phenyl.

27. The process of claim 26, wherein said co-catalyst is $[PhNHMe_2][B(C_6F_5)_4]$.

28. The process of claim 20, wherein M is Zr.

29. The process of claim 28, wherein each $R^1$ is methyl.

30. A process for preparing a polyolefin, comprising:

reacting an olefin with an activated olefin polymerization catalyst composition, under conditions that result in the formation of a polyolefin;

wherein said catalyst composition comprises the pre-catalyst of claim 1.

31. The process of claim 30, wherein said catalyst composition further comprises a co-catalyst having one of the formulae:

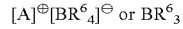

wherein $A^\oplus$ is a cationic Lewis or Brønsted acid.

32. The process of claim 31, wherein said co-catalyst is $[PhNHMe_2][B(C_6F_5)_4]$.

33. The process of claim 30, wherein said olefin is ethene, propene, 1-butene, 1-pentene, 1-hexene, 1-heptene, 1-octene, styrene, alpha-methyl styrene, butadiene, isoprene, acrylonitrile, methyl acrylate, methyl methacrylate, vinyl acetate, vinyl chloride, vinyl fluoride, vinylidene chloride, N-vinyl pyrrolidone, 3-methylbutene, 3-methyl-1-pentene, vinylcyclohexene, vinylcyclobutane, vinylcyclopentane, vinylcyclooctane, 1-decene, enantiomerically pure β-citronellene, 3,5,5-trimethyl-1-hexene or 4-methyl-1-pentene.

34. The process of claim 30, wherein said olefin comprises a mixture of two or more monomers having vinyl unsaturation.

* * * * *